United States Patent [19]

Ollington et al.

[11] Patent Number: 5,403,745
[45] Date of Patent: Apr. 4, 1995

[54] DETERMINATION OF ANALYTES IN BIOLOGICAL FLUIDS IN THE PRESENCE OF SUBSTANCES INTERFERING WITH ASSAYS THEREFOR

[75] Inventors: James F. Ollington, Chelmsford; Ronald J. Byrnes, West Bridgewater, both of Mass.; Donald E. Pogorzelski, Nashua, N.H.

[73] Assignee: Genzyme Corporation, Cambridge, Mass.

[21] Appl. No.: 515,596

[22] Filed: Apr. 27, 1990

[51] Int. Cl.[6] ............... C12Q 1/60; G01N 33/543
[52] U.S. Cl. ........................... 435/11; 422/58; 422/61; 422/72; 435/7.4; 435/17; 435/22; 435/26; 435/962; 436/71; 436/518; 436/528; 436/531; 436/536; 436/538; 436/539; 436/541; 436/807; 436/824; 436/825
[58] Field of Search ............... 422/58, 61, 72; 435/7.4, 11, 17, 22, 26, 962; 436/825, 12, 13, 15, 518, 539, 541, 531, 528, 71, 824, 807, 808, 536, 538, 45

[56] References Cited

U.S. PATENT DOCUMENTS

| | | | |
|---|---|---|---|
| 3,932,221 | 1/1976 | Pfleiderer | 435/26 |
| 3,963,441 | 6/1976 | Dietrich | 436/809 |
| 4,244,694 | 1/1981 | Farina et al. | 422/72 |
| 4,427,769 | 1/1984 | Adlercreutz et al. | 422/61 |
| 4,746,605 | 5/1988 | Kerscher et al. | 435/28 |
| 4,900,662 | 2/1990 | Shah et al. | 436/524 |
| 4,937,199 | 6/1990 | Griffiths et al. | 436/518 |
| 4,946,796 | 8/1990 | Collet-Cassert et al. | 436/513 |
| 5,030,555 | 7/1991 | Clemmons | 436/531 |
| 5,079,170 | 1/1992 | Rosman et al. | 422/58 |

OTHER PUBLICATIONS

Delahunty et al, "Automated Creatine Kinase–MB Estimation by Immuno–Inhibition: A Clinical Evaluation", Clin. Chem., 26 May, 1980, pp. 568–572.

Primary Examiner—Toni R. Scheiner
Assistant Examiner—Christopher L. Chin
Attorney, Agent, or Firm—Bromberg & Sunstein

[57] ABSTRACT

A method is provided, in one embodiment, for the determination of an analyte in a biological fluid sample in the presence of a substance interfering with an assay for the analyte. This embodiment is implemented by using antibodies to cause the selective immunoreaction of at least one of the analyte or the interfering substance and then conducting an assay for the analyte in at least one of the immunoreactants or the non-reactants. Another embodiment provides a disposable reaction device to implement the method. The invention is applicable to the detection of a wide variety of analytes, including cholesterol in a targeted lipoprotein class in the presence of cholesterol in another class; to targeted isozymes of enzymes such as creatine kinase, lactate dehydrogenase, amylase, and alkaline or acid phosphatases in the presence of other isozymes; as well as to targeted immunoglobulins in the presence of non-targeted immunoglobulins.

16 Claims, 13 Drawing Sheets

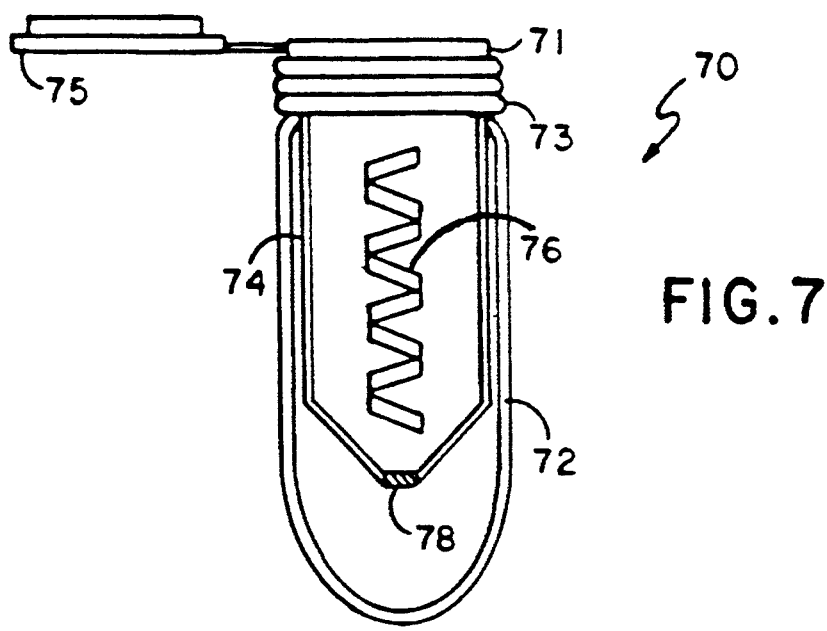
FIG. 7
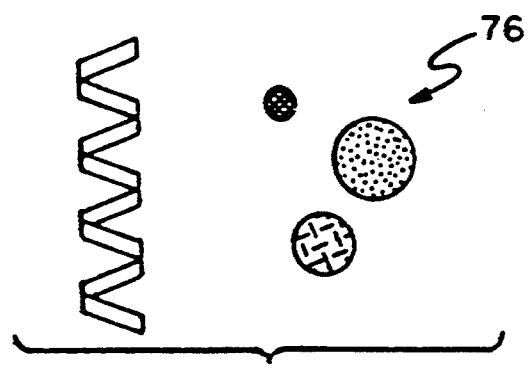
FIG. 8
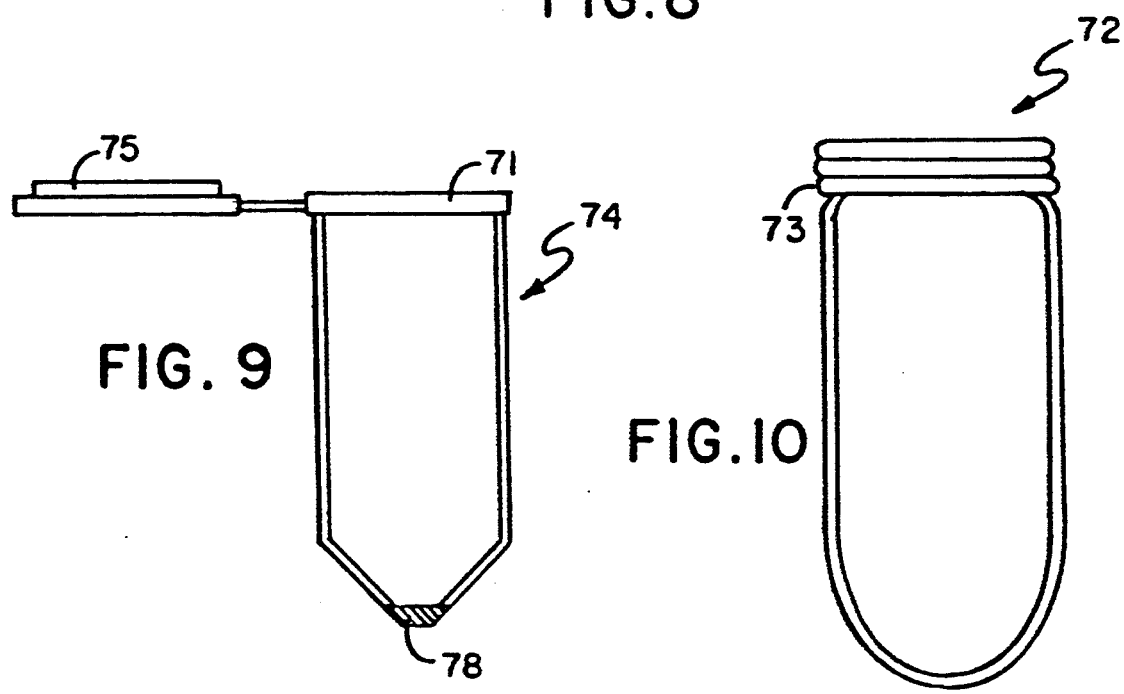
FIG. 9
FIG. 10

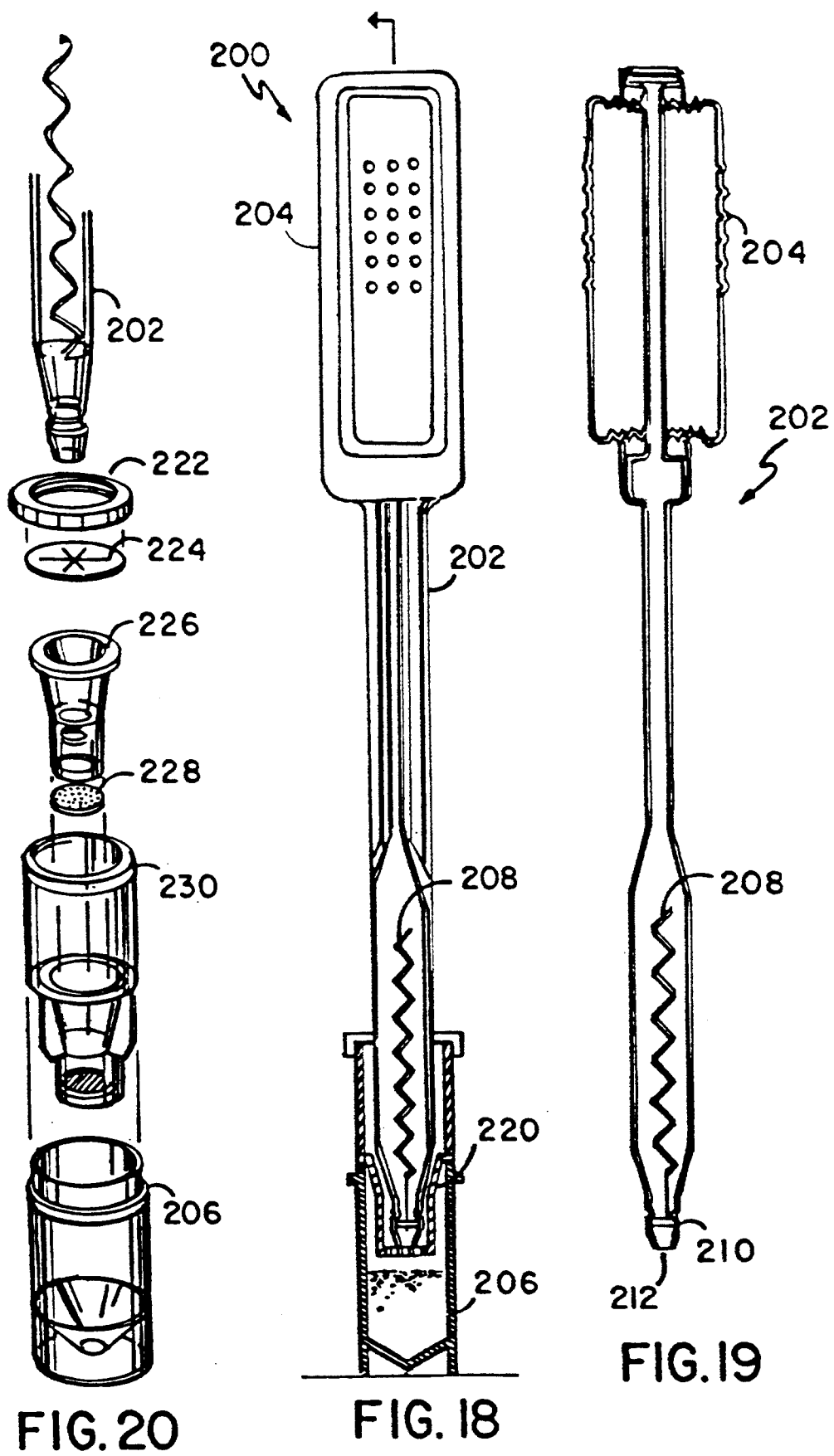

DETERMINATION OF ANALYTES IN BIOLOGICAL FLUIDS IN THE PRESENCE OF SUBSTANCES INTERFERING WITH ASSAYS THEREFOR

TECHNICAL FIELD

The present invention relates to the determination of analytes in the presence of substances interfering with assays for such analytes. The invention also relates to the use of devices for implementing such determination. The invention can be used for the detection, in a biological fluid sample, of analytes in targeted lipoprotein classes; and targeted isozymes of creatine kinase, lactate dehydrogenase, amylase, and alkaline or acid phosphatases; and targeted immunoglobulins; as well as other analytes.

BACKGROUND ART

A. General

Modern medical practice typically requires routine clinical tests of sera and urine for biological analytes such as cholesterol, enzymes (such as creatine kinase, lactate dehydrogenase, acid phosphatase, alkaline phosphatase, amylase, etc.), immunoglobulins, as well as other substances.

More specific (and, typically, more time-consuming) diagnostic tests are also performed in addition to routine tests. For example, the detection of certain isozymes of acid phosphatase is used clinically as an indicator of prostatic cancer as well as various leukemias. Levels of certain isozymes of alkaline phosphatase detected in a blood or serum sample serve as an indicator of bone and liver metabolic activity. Levels of pancreatic specific amylase are an indicator for pancreatitis. Serum levels of the MB isozyme of creatine kinase (CRMB), as well as levels of isozymes of lactate dehydrogenase, are indicators of myocardial infarction (Noel, S. et al. "Enzymes" in *Clinical Chemistry* (Kaplan, L. and Pesce, A., eds. The C. V. Mosby Company, St. Louis, Mich.); pp. 454–483 (1989)). Similarly, the detection of cholesterol, in specific lipoprotein classes, is used in the determination of coronary heart disease risk. (Russel et al. "Lipids" in *Clinical Chemistry* (Kaplan, L. and Pesch, A., eds. The C. V. Mosby Company, St. Louis, Mich.); pp. 968–1004 (1989)). These more specialized tests are often directed to a specific class of analyte that is already the subject of routine tests.

The efficacy of assays for analytes in a biological fluid sample can be reduced due to the presence of substances which interfere with the assay (Kaplan, L. and Pesce, A., "Interferences in Chemical Analysis" in *Clinical Chemistry* (Kaplan, L. and Pesce, A., eds., The C. V. Mosby Company, St. Louis, Mich.); pp. 808–819 (1989)). For example, compounds such as hemoglobin or bilirubin, which have a strong visible absorbance, can interfere with a spectrophotometric assay for an analyte. Kaplan and Pesce, id.

Clinical testing, in the case of both routine and more specialized tests, demands strict adherence to carefully developed quality assurance and quality control procedures in order to assure accuracy and to minimize variability of test results. Concerns over variability and inaccuracy of test results have in fact led to further regulation of clinical laboratories by the Health Care Financing Administration of the U.S. Department of Health and Human Services. 53 Federal Register 29590–29632 (Friday, Aug. 5, 1988) (proposed amendments to 42 CFR part 74 et seq.); 55 Federal Register 9538–9610 (Wednesday, Mar. 14, 1990) (revision of laboratory regulations, final rule with request for comments). These new regulations impose additional burdens on clinical testing laboratories. Such laboratories thus have a need for testing procedures that can be readily verified for adherence to quality control standards. The more specialized tests (as opposed to the routine tests) may readily permit verification, but the inherently sophisticated nature of these tests requires mastery by the laboratory technician of a set of testing protocols entirely different from those used in connection with routine tests. The result is that quality control of such specialized tests typically requires more extensive laboratory procedures and training of laboratory personnel.

An additional complication is posed in the interpretation of test results, even assuming that there is good quality control from one test run to another. For example, because of the important diagnostic information gained from cholesterol results and the need to eliminate interlaboratory variability, uniform cholesterol cutpoints based on national population studies have been adopted. Additionally, a national reference system for cholesterol has been developed so that cholesterol measurements are standardized and values are therefore traceable to the National Reference System for Cholesterol. Due to the absence of accepted National Reference Systems for triglycerides, lipoproteins, and apolipoproteins, much remains to be done in the elimination of interlaboratory variability associated with these lipid related tests. Presently, these tests and other specialized tests for cholesterol may not be directly related to the National Reference System for Cholesterol.

With this discussion as background, the remainder of this Background Art section discusses cholesterol determination, as an example of the state of the art in the detection of analytes in biological fluids. The prior art known to the inventors lacks an assay, for cholesterol in specific lipoprotein classes, that is simultaneously (i) easily interpretable from an epidemiological point of view; (ii) easily, quickly and inexpensively implemented, and (iii) universally applicable to all routine clinical chemistry testing systems. Indeed, the inventors are unaware of any assays, for specific classes of an analyte that are the subject of the routine tests described above, that meets these two criteria.

B. Cholesterol

Biochemical Background

Triglycerides and cholesterol are transported in the blood via lipoprotein particles. Abnormalities in these lipoproteins, either inherited, environmentally contributed, or a combination of both, lead to a variety of disorders including a predisposition to premature coronary heart disease (CHD) and atherosclerosis (N.I.H. Publication Number 88–2925 (1988); and Schaefer and Levy, The New England Journal of Medicine 312:1300–1310 (1985)). The underlying cellular and genetic mechanisms of many of the disease states have been intensively and elegantly explored in the preceding 30 years (Brown and Goldstein, Science 232:34–47 (1986), and Lusis, J. Lipid Research 29:397–428 (1988)).

The chemistry, biosynthesis, function, metabolism, cell biology, and molecular genetics of lipoprotein particles have been extensively reviewed (Segrest, Jere P., and Albers, John J., editors, 128 Methods in Enzymology (1986) and Albers, John J., and Segrest, Jere P., editors, 129 Methods in Enzymology (1986)).

Lipoprotein particles are divided into four major classes based on their density, composition, and electrophoretic mobility: The classes are chylomicrons, very low density lipoproteins (VLDL), low density lipoproteins (LDL) and high density lipoproteins (HDL). LDL and HDL particles may be further subdivided on the basis of density. The lipoprotein particles are composed of triglycerides, cholesterol, fatty acids esters of cholesterol, phospholipid and protein. The varying ratios of protein to lipid, in different lipoprotein classes, account for the physical differences by which these particles can be fractionated by density gradient centrifugation.

The protein components, known as apolipoproteins, are responsible for a variety of cellular functions. Increased levels of LDL cholesterol and decreased levels of HDL cholesterol have been shown to be risk factors for CHD. Consequently, clinical diagnostic assays for cholesterol content in the major lipoprotein classes are performed extensively and a large body of statistical data on the normal ranges for these classes is available standardized by the Centers for Disease Control (McNamara and Schaefer, Clinica Chimica Acta 166:1–8 (1987)).

Cholesterol Determination

In the clinical laboratory, the following assays are performed routinely to characterize the lipid and cholesterol profile of a plasma or serum sample: (i) Triglycerides are determined using the enzyme lipase(s) plus enzymes linked to a color indicator system, (ii) Total cholesterol is determined enzymatically using cholesterol esterase, cholesterol oxidase and other enzymes and reagents which translate the oxidation of cholesterol into a detectable color change, and (iii) HDL cholesterol is determined enzymatically as for (ii) above in the supernatant of a sample following selective precipitation of the VLDL and LDL fractions using a mixture of polyanions, e.g. sulfated polysaccharides, or phosphotungstate and divalent cations (Burstein et. al., J. Lipid Research 11:583 (1970); and Mulder et. al. Clinica Chimica Acta 143:29–35 (1987)). VLDL and LDL cholesterol (VLDL.C, LDL.C) are measured indirectly using the Friedewald equation (Friedewald et. al., Clin. Chem. 18:499–502 (1972)):

Total cholesterol=HDL.C+VLDL.C+LDL.C
LDL.C=Total.C−(VLDL.C+HDL.C)
LDL.C=Total.C−(Triglycerides/5+HDL.C)

The equation assumes (i) that no chylomicrons are present, for example, in a blood sample from a fasting patient, and (ii) that there is a constant relationship between cholesterol and triglycerides: This is known to be untrue in hypertriglyceridemic conditions (Cohn et. al., Clinical Chemistry 34:2456–2459 (1988); and Rao et. al., Clinical Chemistry 34:2532–2534 (1988)).

Thus the above analytical procedures suffer from several disadvantages. (i) The VLDL.C and LDL.C are not measured directly but rather are estimated using a formula. (ii) The Friedewald formula is known to be imprecise under conditions of clinical relevance i.e. elevated triglyceride levels (>400 mg/100 ml) (Cohn et. al., Clinical Chemistry 34:2456–2459 (1988); and Rao et. al., Clinical Chemistry 34:2532–2534 (1988)). (iii) HDL.C determination relies on the selective precipitation of VLDL and LDL particles by a polyanion, or by phosphotungstate, plus divalent cations, with subsequent total cholesterol measurement of the separated supernatant. In general, cholesterol detection in specific lipoprotein classes lacks a standardized reference system.

Mulder et. al. (Clinical Chimica Acta 143:29–35 (1987)) report on the direct measurement of cholesterol in redissolved LDL precipitates but such measurements are not performed in routine diagnostic surveys.

More recent efforts toward separation and quantitation of lipoprotein classes have utilized antibodies, either polyclonal or monoclonal, directed against apolipoproteins which are specific to distinct, clinically relevant lipoprotein particles (Tikkanen et. al., J. Lipid Research 24:1494–1498 (1983); and Ordovas et. al. J. Lipid Research 28:1216–1224 (1987)).

In research laboratories a variety of immuno-based analytical techniques have been employed to quantitate lipoproteins, including radial immunodiffusion, radioimmunoassay and electroimmunoassay, but these techniques are too cumbersome to be employed in a clinical diagnostic setting where large numbers of samples must be handled rapidly. This disadvantage may be addressed by using an enzyme-linked immunoabsorbant assay (ELISA), and this is an area of active investigation (Ordovas et. al., J. Lipid Research 28:1216–1224 (1987)).

However, there is a further disadvantage which some of these immuno-based techniques, including ELISA suffer, and that is that these procedures quantitate an epitope associated with specific lipoprotein classes—they do not measure cholesterol levels. The significance of this situation is that there must be a very large number of samples analyzed by an immuno-based procedure to establish its correlation with cholesterol values (measured enzymatically) and which are interpretable epidemiologically. Thus, ELISA-based tests require a long lead time to gain acceptance in the clinical diagnostic industry.

Methods which utilize immobilized antibodies to measure levels of substances in biological fluids are known. Longenecker (U.S. Pat. No. 4,302,536 (1981)) reported the determination of antigenic materials in biological fluids and cells by colorimetric immunoassay with an adduct of antibody and chromo-protein. Onishi and Ito (Eur. Pat. No. 327,918 (1989)) reported an immunoassay using the homogeneous competitive reaction between a target and labelled substance and a specific binder. Freytag and Ishikawa (U.S. Pat. No. 4,657,853 (1987)) reported a high sensitivity immunoassay using a polymeric enzyme-antibody conjugate. Nippon (Jap. Pat. No. 59226864 (1984)) reported an immunoassay in which levels of transforming growth factor (TGF) in a liquid sample are detected using an immobilized TGF antibody and an enzyme labelled TGF antibody. Gomez and Wicks (U.S. Pat. No. 4,353,982 (1982)) report an immunoassay for creatine kinase in blood serum using iodine-125 labelled antibody to precipitate immune complex mixtures.

Several groups have examined selective immunoprecipitation of specific lipoprotein classes followed by cholesterol quantitation in the lipoprotein class remaining in solution. Heuck et al. reported the use of antibodies to ApoB to precipitate LDL and VLDL followed by measuring cholesterol levels in the HDL left in the supernatant. Antibodies to apoAI and apoC were also used, to precipitate HDL and VLDL, followed by determination of cholesterol levels in the LDL left in the supernatant. (Heuck et al. Clin. Chem. 31:252–258 (1985)). Kerscher et al. reported the use of antibodies to HDL to precipitate HDL and VLDL, followed by centrifugation to separate the precipitate, followed by analysis of cholesterol levels, or other component levels, in the LDL in the supernatant (Kerscher et al. U.S. Pat. No. 4,746,605 (1988); Fed. Rep. Germany Patent No. P32 15 310 (1983); Kerscher et al. Clin. Bioch. 18:118–125 (1985)). Antibodies to both apoproteins and whole lipoproteins, including immobilized antibodies, have been used to immunoprecipitate lipoproteins followed by determination of the cholesterol content of the lipoprotein class remaining in solution (Ziegenhorn et al. Canadian Patent No. 1 211 707 (1986)). This reference, however, does not describe any specific structure or device on which the antibodies are immobilized.

SUMMARY OF THE INVENTION

The invention disclosed herein provides in one embodiment a method for detecting an analyte in a biological fluid sample in the presence of a substance interfering with an assay for the analyte. This embodiment is implemented by using antibodies to cause the selective immunoprecipitation of an interfering substance and then conducting an assay for the analyte the non-reactants. In another embodiment, the invention provides a disposable reaction device to implement the method.

The invention is applicable to the detection of a wide variety of biological analytes, including but not limited to cholesterol in a targeted lipoprotein class in the presence of cholesterol in another class; as well as to targeted isozymes of creatine kinase, lactate dehydrogenase, amylase, alkaline or acid phosphatase in the presence of non-targeted isozymes; and targeted immunoglobulins in the presence of non-targeted immunoglobulins.

BRIEF DESCRIPTION OF THE DRAWINGS

The foregoing features of the invention will be more readily understood by reference to the following detailed description taken with the accompanying drawings, in which:

FIG. 7 is a vertical section of a reaction device in accordance with the embodiment of the invention described in Example 2.

FIG. 8 illustrates a variety of solid support matrices for antibody immobilization in accordance with the invention.

FIG. 9 is a vertical section of the inner reaction chamber 74 of the reaction device 70 of FIG. 7.

FIG. 10 is a vertical section of the outer collection chamber 72 of FIG. 7.

FIG. 18 is a cut away view of an embodiment of a reaction device similar to that of FIG. 11, but with certain enhancements.

FIG. 19 is a vertical section of the reaction pipette 202 of FIG. 18.

FIG. 20 is an exploded view of the filter unit 220 of FIG. 18 with related components.

DETAILED DESCRIPTION OF SPECIFIC EMBODIMENTS

Figure 1:
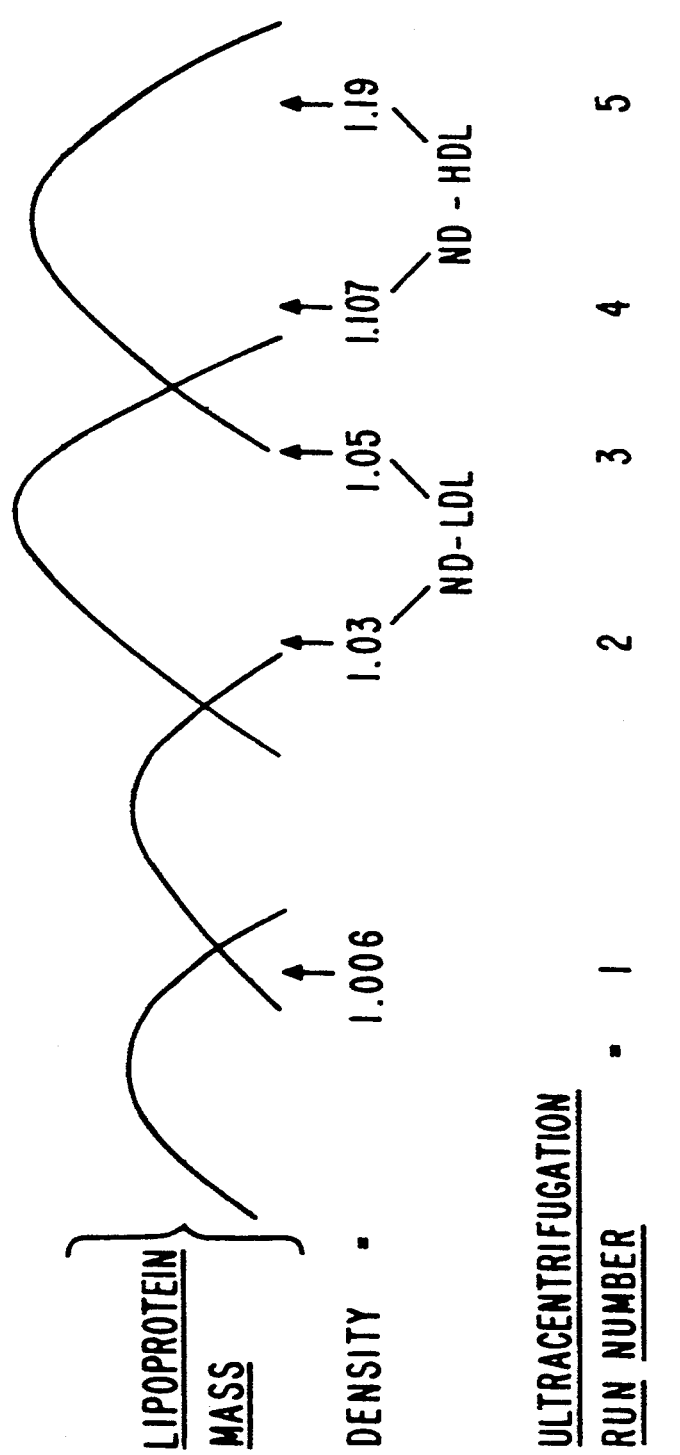
FIG. 1 is a schematic illustration of the sequential density gradient ultracentrifugation separation of the lipoproteins used as antigens for obtaining antisera used in Example 1.

The invention provides, in one embodiment, a method for the detection of an analyte in a biological fluid sample, in the presence of a substance interfering with an assay for such analyte, using immunoseparation technology. In the invention, antibodies are used to cause selective immunoreaction of a substance interfering with an assay for the analyte, and then the analyte is detected by assay of the non-reactants. In one embodiment of the invention, a reaction device is used to rapidly and inexpensively implement the immunoreaction-separation. The antibodies used in the immunoreaction may be freeze dried or used as a preparation on a suitable carrier. A wide range of suitable carriers and separation techniques for this purpose are available. Thus the antibodies may be bound to the surface of an insoluble carrier whose mass, density, surface area or charge will facilitate separation of immuno-reactants from non-reactants. Examples of insoluble carriers are microporous beads, latex particles, magnetic particles, controlled pore glass, gel matrices from cross linked dextran, cross linked polysaccharides, or cross linked acrylamide, microporous filters or membranes. Other suitable insoluble carriers include a coiled strip or the interior wall of the reaction device itself. Antibodies may also be bound to soluble large MW polymers to effect a more readily precipitable immune complex with the analyte. Examples of suitable polymer carriers are polysaccharides, proteins or polynucleotides. This approach can also enhance the kinetics of the immunoseparation. The immuno-precipitating antibodies may be either polyclonal or monoclonal or mixtures of either or both, provided they possess sufficient specificity, lack of cross-reactivity, ability to quantitatively absorb to a broad range of substrate concentrations, and separability of the immuno-reacted complexes.

Purification of an analyte in a biological fluid sample using the invention permits the enhancement of the efficiency of existing routine diagnostic tests currently in clinical use. The invention also provides a systematic way of making these routine tests more specific; such specific tests can replace specialized testing procedures, with the result that the invention assists in achieving the quality control, cost reduction, and availability of tests for specific analytes in a class of analytes.

There are several advantages of the invention, applied to cholesterol testing, over the prior art. Embodiments of the invention may be used in connection with the determination of cholesterol in an immunoseparated lipoprotein class based on conventional enzymatic techniques. Because the invention permits utilization of existing routine clinical tests (applied to the immunoseparated lipoprotein class), the results of testing, in accordance with a preferred embodiment of the invention, may be directly related to the national reference system. (Other immuno-based assays currently provided by embodiments of the invention include apoliproprotein quantitation, for which statistically significant clinical data, i.e., normal ranges in the population, are not yet available.) Thus the analytical data generated by practicing this invention may be directly related to existing data bases, and may foreshorten dramatically the lead time in bringing the benefits of immunospecificity to the cholesterol diagnosis industry. Furthermore, the invention allows for the design of analytical regimens which will provide an internal control on individual cholesterol measurements within the regimen. For example, a plasma or serum sample may be first analyzed for total cholesterol in the absence of any separation of lipoprotein fractions. Subsequently, aliquots of the original sample may be subjected to immunoprecipitation by various specific antibody preparations either sequentially or on separate aliquots of the original sample. In each situation it is possible to validate the testing regimen by summing the cholesterol results of all fractionations and comparing this sum to the unfractionated value. The use of antibodies in the invention permits highly specific fractionation of lipoprotein classes.

In the practice of the invention, mixtures of poly- and monoclonal antibodies are feasible. The antibodies need not be optimized for characteristics relevant to other immuno-based techniques, e.g., good binding to plastic surfaces as needed for ELISA procedures. In addition, assay in accordance with this invention may be implemented with a device containing stabilized antibodies, which allows rapid, inexpensive, and efficient analysis. It is universally applicable to all routine clinical testing systems.

The embodiments described below are discussed principally in the context of the detection of cholesterol in specific lipoprotein classes. However, as shown below, the invention is equally applicable to the detection of a wide variety of other analytes.

A. Antigen Preparation

1. Narrow density lipoprotein fractions

Pooled human plasma in CPD, collected at the New England Medical Center Blood Bank, was used for the preparation of lipoprotein fractions for use as antigens. The plasma, at an assumed density of 1.006 (g/ml), was fractionated by sequential ultracentrifugation as follows:

8×38 ml plasma+1 ml KBr at 1.006 density were loaded into Beckman quickseal tubes and spun for 18–22 hr @ 4° C., 45 k rpm in a Ti60 rotor. Following centrifugation the tubes were stored on ice and the 1.006 floating lipoprotein fraction was sliced off the top of the tube, cutting close to the lower interface. The 1.006 bottom fractions were pooled and gravity filtered through a Whatman filter (grade #1). The filtrate volume was measured and the density adjusted to 1.03 solid KBr (vacuum oven-dried) according to formula 1:

$$gKBR = \frac{Vi(Df - Di)}{1 - (v \cdot Df)} \quad (1)$$

Vi = Initial volume;
Df = Final density
Di = Initial density
v = Partial specific volume of KBr The second ultracentrifugation of plasma (now at 1.03) density) was carried out under the same conditions as above and the tubes, again maintained on ice post-centrifugation, were sliced to remove the upper fraction. The 1.03 bottom fractions were pooled, filtered as before and adjusted to a density of 1.05 g/ml according to formula 1. The third ultracentrifugation run was performed under the same conditions as above and the collected tubes were maintained on ice prior to slicing off the top lipoprotein layer. This top layer was sliced just at the lower interface; the 1.05 top layers were pooled and contain the LDL fraction referred to as narrow density LDL (ND-LDL).

The 1.05 bottom fractions were pooled, filtered as before and the density adjusted to 1.107 with KBr (formula 1). This material underwent ultracentrifugation number 4 under the following conditions: 4° C., 50 k rpm, 42–48 hr in a Ti60 rotor. The collected tubes were maintained as described above and the upper lipoprotein fraction was sliced off close to the lower interface. The 1.107 bottom fractions were pooled, filtered and the density adjusted to 1.19 (formula 1); this fraction underwent ultracentrifugation number 5 under the same conditions as run 4. The collected tubes were sliced close to the lower interface of the top layer to yield a 1.19 top fraction containing narrow density HDL (ND-HDL). The fractionation of the lipoprotein particles through sequential ultracentrifugation is summarized schematically in FIG. 1. The harvested narrow density fractions were washed and refractioned by repeated ultracentrifugation. The ND-LDL (1.05 top fraction) was respun at a density of 1.05 @ 4° C., 18–22 hr, 45 k rpm, in a Ti60 rotor; the top fraction was collected, respun, collected and respun and finally harvested and dialyzed vs. PBS. Typically, 20–25 ml of refractionated ND-LDL is dialyzed into 3.0 PBS for 18 hr at 4° C. The PBS formula is as follows:

| 10 × Stock | = Soln. A = | 80 g NaCl |
|---|---|---|
| | | 2.0 g KCl |
| | | 1.97 g $CaCl_2 \cdot 6H_2O$ |
| | | 1.0 g $MgCl_2 \cdot 6H_2O$ |
| | | 0.01 g $NaN_3$ in 1.0 L |
| | | deionized $H_2O$ |
| | = Soln. B = | 11.5 g $Na_2HPO_4$ |
| | | 2.0 g $KH_2PO_4$ |
| | | 0.01 g $NaN_3$ in 1.0 L |
| | | deionized $H_2O$ |

| Final PBS Soln.: | 100 ml Soln. A + 100 ml Soln. B |
| --- | --- |
| | Bring to 900 ml with deionized H$_2$O |
| | Adjust to pH 7.4 with 1N NaOH |
| | Adjust to 1.0 L final volume |

The ND-HDL fraction (1.19 top) was respun in an ultracentrifuge at a density of 1.107 @ 4° C., 50 k rpm, 48 hr in a Ti60 rotor; the top fraction was collected and respun under the same conditions. Finally the upper fraction was dialyzed vs. PBS; typically 10–15 ml into 3.0L PBS @ 4° C. for 18 hr.

The purity of the dialyzed narrow density fractions was checked by electrophoresing an aliquot over a 4–22.5% polyacrylamide gradient gel under denaturing conditions using the system described essentially by Laemmli (1970). The protein content of each fraction was determined by the standard methods of either Lowry or using the Biorad reagents. The preparation of narrow density lipoprotein fractions described above is an improvement on the method described by Schumaker, V. N. and Poppione, O. L. (1986) Methods in Enzymology, Vol. 128 pp. 155–170.

The yields of narrow density lipoprotein fractions isolated in this manner are typically: from 266 ml plasma, 31 ml of ND-LDL at 1.2 g/ml protein and 12 ml ND-HDL at 2.5 mg/ml protein are obtained.

2. Purification of Apoproteins

Starting with purified ND-LDL, ApoB was isolated by electrophoresis through a preparative 15% polyacrylamide gel followed by excision of the separated ApoB band. Upon completion of electrophoresis the gel was stained with sodium acetate to visualize protein bands, as described in E. Harlow and D. Lane, editors, *Antibodies. A Laboratory Manual* (Cold Spring Harbor Press, 1988). The ApoB containing gel region was excised using a scalpel or razor and the polyacrylamide gel was homogenized by repeated passages though progressively narrower gauge needles according to the method described essentially in *Antibodies, ibid.* The ApoB in homogenized acrylamide may be stored at @ 4° C. prior to immunization.

Starting with approximately 10 ml purified ND-HDL, ApoAI and ApoAII were purified by chromatography over Sephacryl S-200 essentially as described by Brewer, et al. (1986), Methods in Enzymology 128:223–246. Fractions containing separated ApoAI and AII were quantitated for protein by Biorad assay and electrophoresed through a preparative 15% polyacrylamide gel under denaturing conditions. Protein bands were visualized, excised and prepared for immunization as described above.

B. Immunization

1. Narrow density LDL fraction: One ml of a 1 mg (protein)/ml solution mixed in an equal volume of Freund's complete adjuvant was used to inject goats intramuscularly. At roughly 2–4 week intervals the goats received booster injections of first, 1 mg protein (equivalent) in incomplete Freund's adjuvant, followed by 0.5 mg protein (equivalent) in incomplete Freund's adjuvant.

Apoprotein B in homogenized polyacrylamide, prepared as described above, was used to maintain high antibody titre via injections of approximately 0.5 mg of Apo B in incomplete Freund's adjuvant every 2–3 weeks.

2. Narrow density HDL fraction: 0.5 mg of a 5 mg (protein)/ml solution mixed in an equal volume of complete Freund's adjuvant and was used for the primary goat immunization. The first boost utilized 0.5 mg of the 5 mg/ml solution in an equal volume of incomplete adjuvant and the second boost used 50% of the above level of immunogen.

It is within the scope of the invention to use purified ApoAI and ApoAII to immunize individual goats, and obtain the corresponding antisera.

Similarly, it is within the scope of the invention to use purified ApoCI-III to supplement the narrow density HDL immunogen.

Furthermore, it is within the scope of the invention to use purified ApoE both individually and as a supplement to narrow density HDL to immunize goats, by standard immunological techniques, and to obtain corresponding antisera.

C. Antisera Characterization and Purification

Approximately 2–10 ml of serum were prepared from initial test bleeds following booster injections. The antisera was characterized by Western blot (as described below) against isolated VLDL, LDL, HDL, and whole human plasma. By this method, the anti-narrow density LDL sera was shown to be free of material cross-reactive to any of the apoproteins of purified HDL. The ND-LDL antisera showed cross-reactivity only to ApoB in VLDL, LDL, and whole plasma.

The anti-narrow density HDL sera showed reactivity to ApoAI in HDL and whole plasma and reactivity to ApoCs and ApoE in HDL, VLDL and whole plasma. A small amount of cross-reactive material to ApoB was detected and can be removed by immunoaffinity chromatography over an ND-HDL-sepharose column. The column is prepared in the following manner:

i) Ligand (HDL) Coupling

Weigh out 3 g freeze dried CNBr-activated Sepharose-4B (Pharmacia) powder. Resuspend powder in 11.0 ml 1 mM HCl in a 50 ml centrifuge tube. Wash gel for 15 minutes with 1 mM HCl on a scintered glass filter (slow drip using the vacuum; use 200 ml/g powder). Dialyze the ligand (HDL) in coupling buffer (0.1M NaHCO$_3$, 0.5M NaCl, pH 8.3; 10–20 ml in 2.0L Buffer, overnight at 4° C. and mix with gel in a centrifuge tube overnight on a rocker at 4° C. (use 5 ml coupling buffer/g powder).

ii) Glutaraldehyde Crosslinking

Sepharose-HDL beads are centrifuged at 2000 g for 15 minutes to settle beads or are passed through a scintered glass filter to collect the beads, then the beads are incubated for one hour with 4 vol of solution 2. The beads are collected by filtration or sedimentation, the supernatant is discarded, and the beads are incubated for 1 hour with 4 vol NaHCO$_3$ and glutaraldehyde. The unreacted aldehyde groups are blocked by incubating coupled sepharose in 4 vol. 1M Tris-HCl (pH 7.8 overnight at 4° C.).

The sepharose is then collected and washed with three cycles of alternating pH, each cycle being: 0.1M acetate buffer pH 4.0, 0.5M NaCl followed by 0.1M Tris pH 8.0, 0.5M NaCl. The sepharose is then suspended and coupled with Buffer A and incubated overnight at room temperature. The sepharose is then collected and resuspended in Buffer A and stored at 4° C.

Solutions

1) NaHCO$_3$, 0.25M pH 8.8
2) 0.015% Glutaraldehyde in Solution 1.
3) 1M Tris HCl, pH 7.8

4) Buffer A 10 mM KPO4 150 mM NaCl 1 mM EDTA 0.1% NP40

ND-HDL IgG was affinity purified over this column essentially by the procedures described by McConathy, W. J. et al. (1985), Cuatrecasas, P. (1970) and Kowal, R., & Parsons, R. G. (1980).

Antisera was characterized further by examining immunoreactivity against lipoprotein particles that had been electrophoresed through an agarose gel under non-denaturing conditions using the Corning Agarose Universal Electrophoresis System ®. Following electrophoresis, 10–20 ml of antisera (control and sample antisera were tested separately) were loaded into the vertical wells in the gel and incubated for approximately 18 hours at ambient temperature in a sealed moist environment. The gel was examined for the presence of opaque precipitin lines to determine the specificity of the sample antisera versus control antisera. The gel was equilibrated in PBS by 1–2 soakings in approximately 200 ml PBS at room temperature with gentle agitation. The gel was the air-dried for 16–20 hours at ambient temperature and stained for protein by Coomassie Blue.

The anti-ND-LDL sera showed cross-reactivity with the Beta migratory lipoprotein region only; no reactivity was detectable either to the alpha migrating region or to albumin.

Antisera was delipidated and the IgG fractions further purified using a combination of standard techniques including ammonium sulfate precipitation, ultracentrifugation, and affinity chromatography either over a protein A or over the appropriate immunoaffinity material (i.e.: ND-HDL or ND-LDL) as described above.

ND-LDL antisera purification was monitored by Western blot by the following procedure. The lipoprotein particles were electrophoresed through an SDS-PAG described above followed by electrotransfer to nitrocellulose (S & S) using the following conditions: 40 volts for 16–18 hours; the transfer buffer is: 20 mM Tris pH 8.3, 150 mM glycine, 20% methanol. ND-LDL antisera was reacted with the nitrocellulose sheet and cross-reactivity was detected using a secondary antibody conjugated with calf intestinal alkaline phosphatase followed by incubation with a phosphatase substrate-chromophore complex; color development was observed visually. These procedures are essentially as described in Vogel, et al. (1979) and Mason, et al. (1978).

Finally, the anti-ND-LDL sera was freeze dried using a Virtis Freezemobile 24 freeze drier at −55° C. to −57° C. to 65 millitorr overnight.

EXAMPLES

Example 1

Immunoprecipitation of Beta lipoproteins in human plasma using anti-ND-LDL sera was examined and compared with the prior art. 200 µl of fresh human plasma was added to a 1.5 ml polypropylene conical tube containing the equivalent of 50 µl of anti-ND-LDL sera prepared essentially as above. The contents were mixed gently and incubated at ambient temperature for 30 minutes followed by centrifugation for 15 minutes in a Beckman microfuge at setting 12. The supernatant was withdrawn and gravity filtered through a cotton wool plugged pipette tip.

Figure 2:
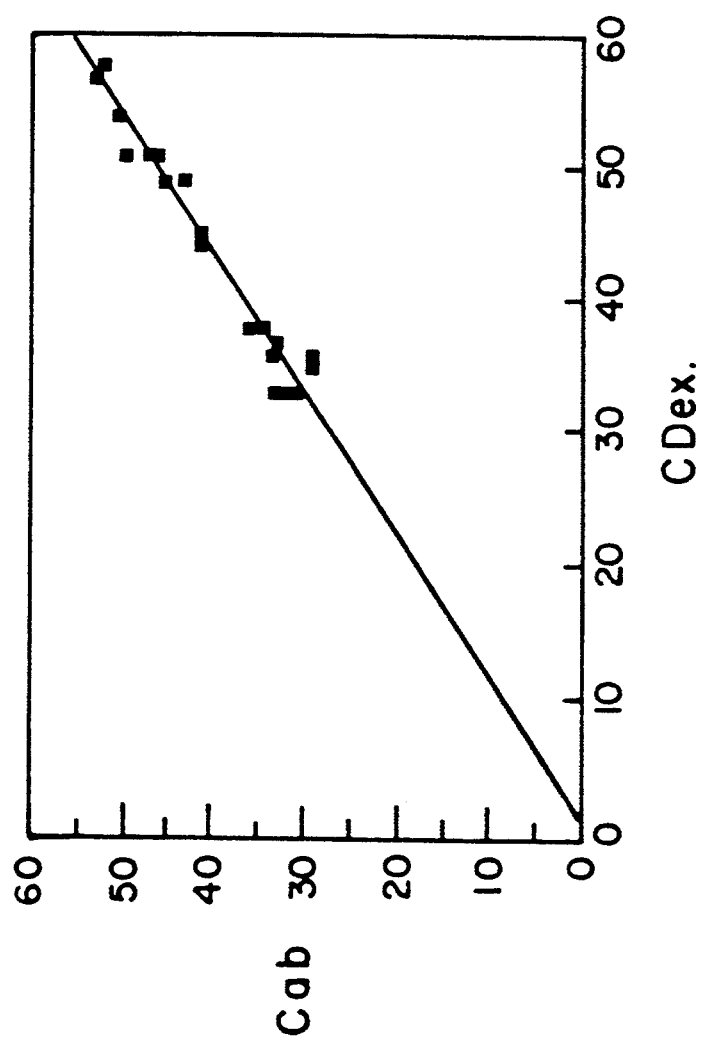
FIG. 2 is a correlation of supernatant cholesterol values between dextran sulfate and anti-ND-LDL sera precipitation method over 19 human plasma samples, in accordance with Example 1.
Figure 3:
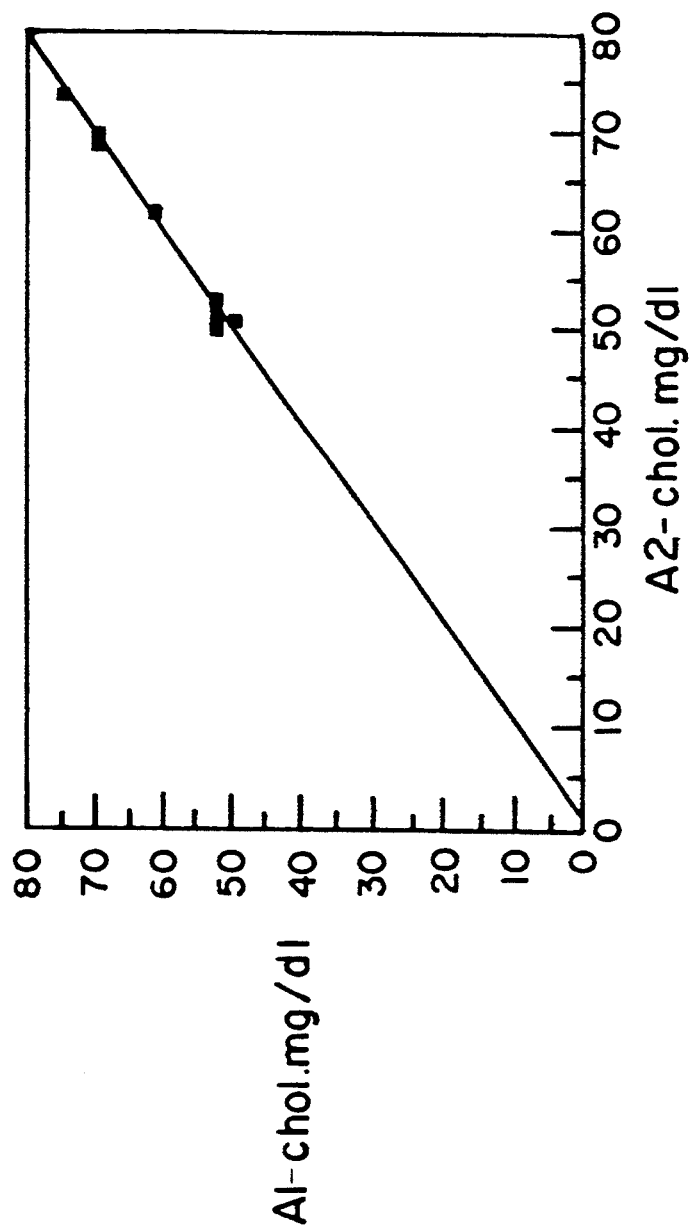
FIG. 3 is a graph showing between-run precision of the immunoprecipitation method over eight human plasma samples, in accordance with Example 1.
Figure 4:
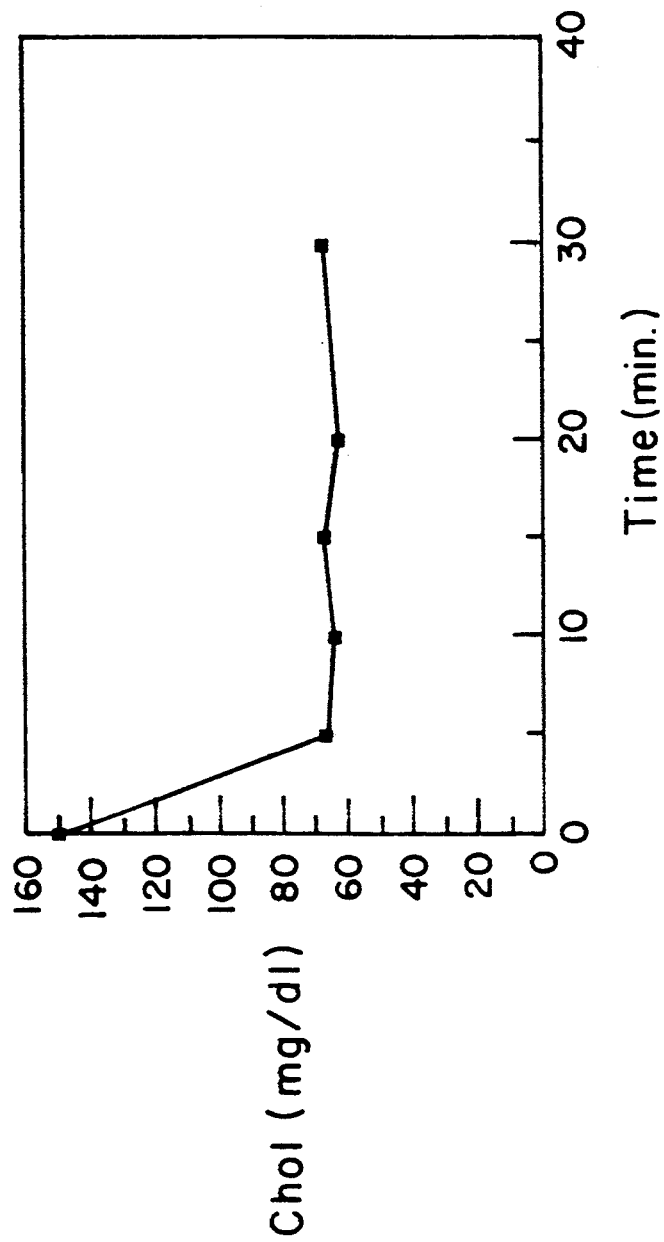
FIG. 4 is a graph showing the time course for the precipitation of human plasma ApoB-containing lipoprotein particles by freeze-dried anti-ND-LDL sera as determined by supernatant cholesterol estimation, in accordance with Example 1.
Figure 5:
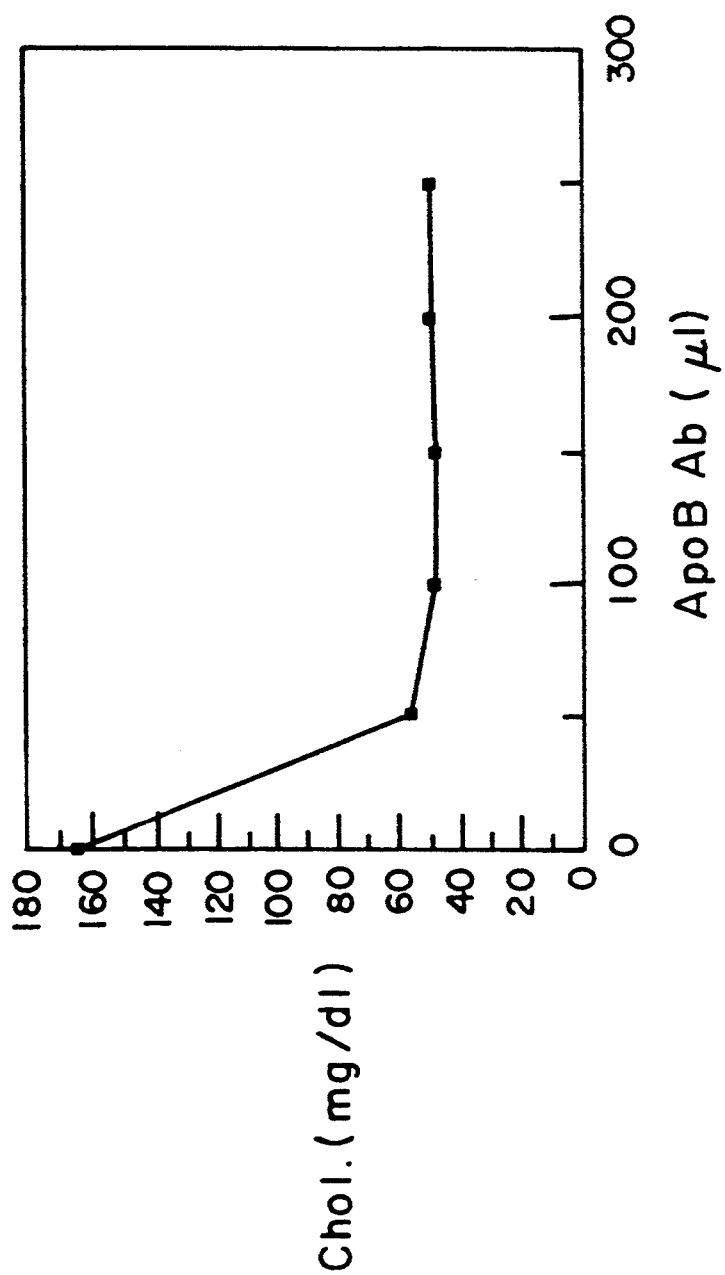
FIG. 5 is a graph similar to that of FIG. 4 but wherein the precipitant is non freeze-dried antisera, in accordance with Example 1.

The filtrate was assayed for total cholesterol using an Abbott ACA 200 chemistry analyzer and Abbott A-Gent cholesterol reagents, although any cholesterol determination method should give equivalent results. FIG. 2 depicts the correlation of immunoprecipitated supernatant (HDL) cholesterol values (mg/dl) for 19 human plasma samples compared with values obtained using dextran sulfate (50 kd molecular weight) as a control Beta lipoprotein precipitating agent, used essentially as described by Warnick, et. al (1985). FIG. 3 indicates the between run precision of the antibody immunoseparation method over 8 human plasma samples tested (in duplicate) on two separate occasions. A separate batch of purified, freeze dried anti-ND-LDL sera was used to examine the time course of the immunoseparation reaction on a human plasma sample. FIG. 4 illustrates the time course results using the equivalent of 300 µl of antisera in the reaction with 200 µl of plasma; the dextran sulfate control supernatant value was 58.5 mg/dl. This same batch of antisera was titred for immunoprecipitation performance on human plasma prior to freeze drying and the results are indicated in FIG. 5; on this plasma the dextran sulfate control value was 42 mg/dl.

Figure 6:
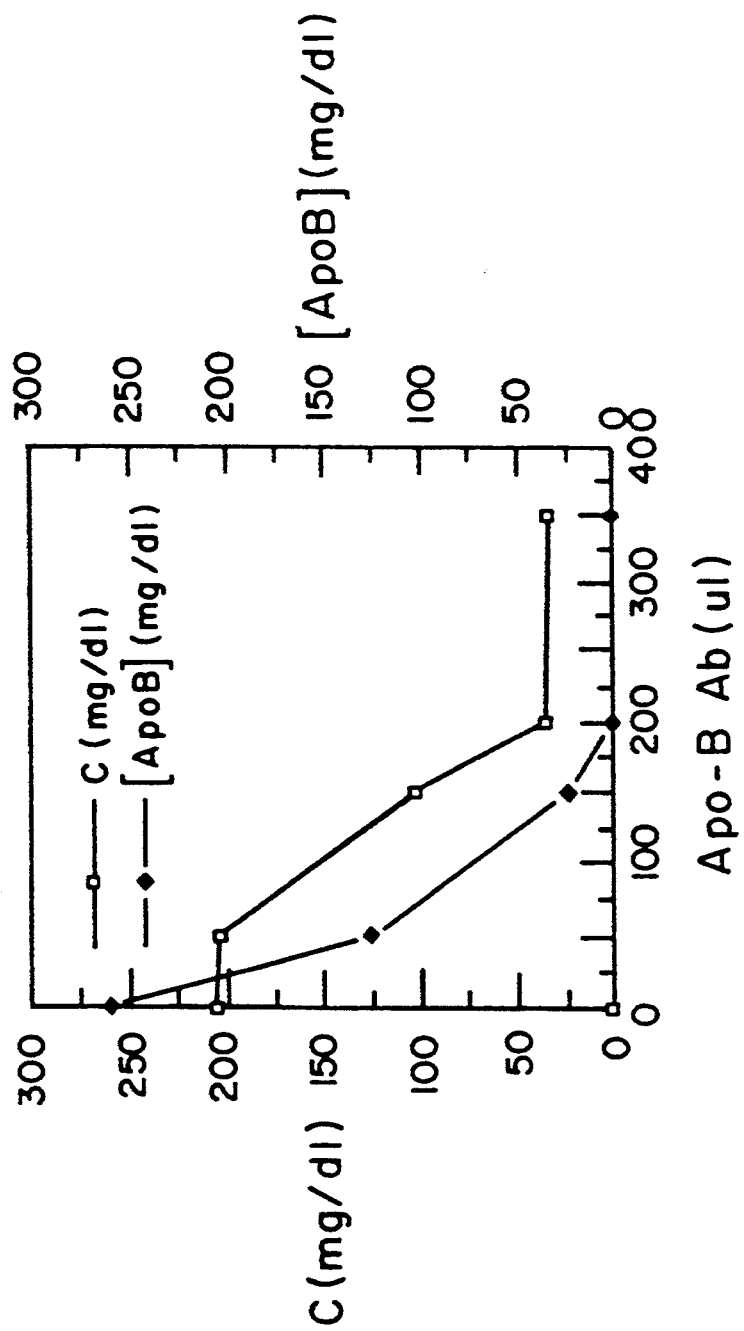
FIG. 6 is a graph supernatant cholesterol and ApoB levels in accordance with Example 1.

Apoprotein immunoassays were used to evaluate the comparative specificity of lipoprotein particle separation between the immunoseparation method and the dextran sulfate method. FIG. 6 demonstrates the immunoprecipitation of lipoprotein particles by anti-ND-LDL sera monitored by the reduction in supernatant (filtrate) cholesterol values (as described above) and by Apoprotein B immunoassay measured by the method of Ordovas, et al. (1987). At the equivalent of 350 µl anti-ND-LDL sera, the supernatant cholesterol value was 32.9 mg/dl, the dextran sulfate control value was 30.0 mg/dl. By immunoassay, the following results were obtained: at 350 µl of antisera the supernatant ApoB level was undetectable above the background control; the dextran sulfate supernatant yielded 1.2 g/dl ApoB remaining in the supernatant.

Example 2

As an alternative to the separation method of example 1, which employs centrifugation of the reacted sample followed by supernatant removal and subsequent filtration, a specialized reaction device may be used in accordance with the invention to achieve both the immunoreaction and separation. FIG. 7 is a schematic illustration of one embodiment of such a device. FIGS. 8, 9 and 10 illustrate individual components of this embodiment. The device has three components: (i) an outer collection chamber 72 (separately shown in FIG. 10) which collects the filtrate at the completion of sample preparation, (ii) an inner reaction chamber 74 (separately shown in FIG. 9) which is supported (for example by a flange 71 forming part of the reaction chamber, resting on the threaded shoulder 73 of the collection chamber 72) within the outer collection chamber 72 and which has a suitable filter material 78 built into its base, and (iii) an immobilized antibody component 76 which may, for example, be antibody-coated, or beads or a coiled strip, such as represented in FIG. 8), which is contained within the reaction chamber 74. Any other suitable means for immobilization of the antibodies may be employed, such as coating them on the interior surface of the reaction chamber 74. The reaction chamber 74 includes a cap 75 that is hingedly attached to the flange 71, so that the reaction chamber 74 may be conveniently capped prior to centrifuging as described below.

The immunoreaction-separation is implemented by the device by pipetting a serum or plasma or blood sample into the reaction chamber 74 (FIG. 7), the cap 75 on the reaction chamber 74 is closed, the sample is mixed with the immobilized antibody and incubated to allow the immunoreaction to occur. At an appropriate time the device is centrifuged, so that the filter retains crude debris and the solid antibody support material, and the non-reactants pass into the collection chamber as filtrate. The reaction chamber may be discarded following centrifugation and the collection chamber may be capped (using a screw cap gripping the threaded shoulder 73 in FIG. 10) or the filtrate or an aliquot thereof may be assayed for non-reactant analyte(s), using routine assays.

Example 3

Figure 11:
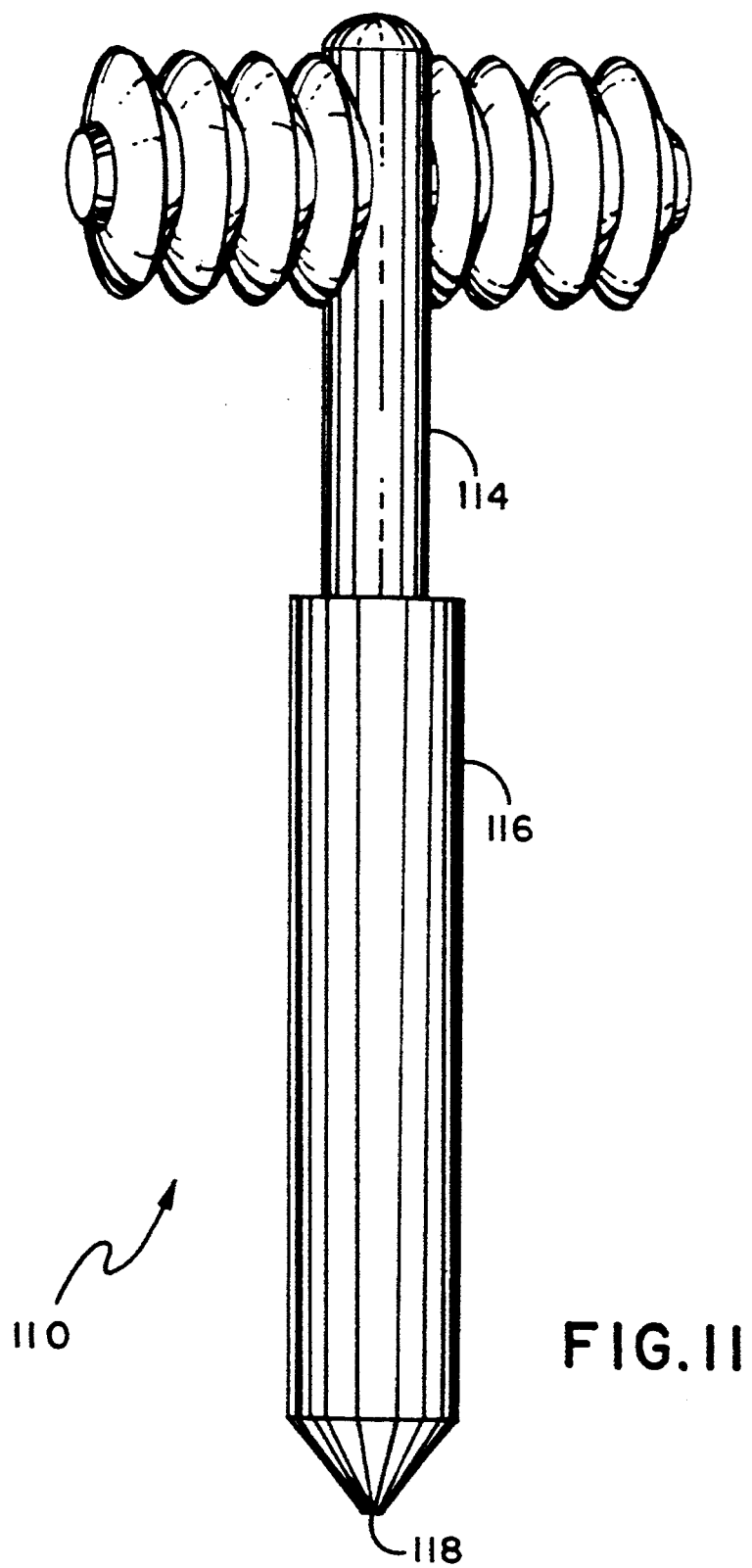
FIG. 11 is a perspective view of another embodiment of a device in accordance with the invention as described in Example 3.
Figure 12:
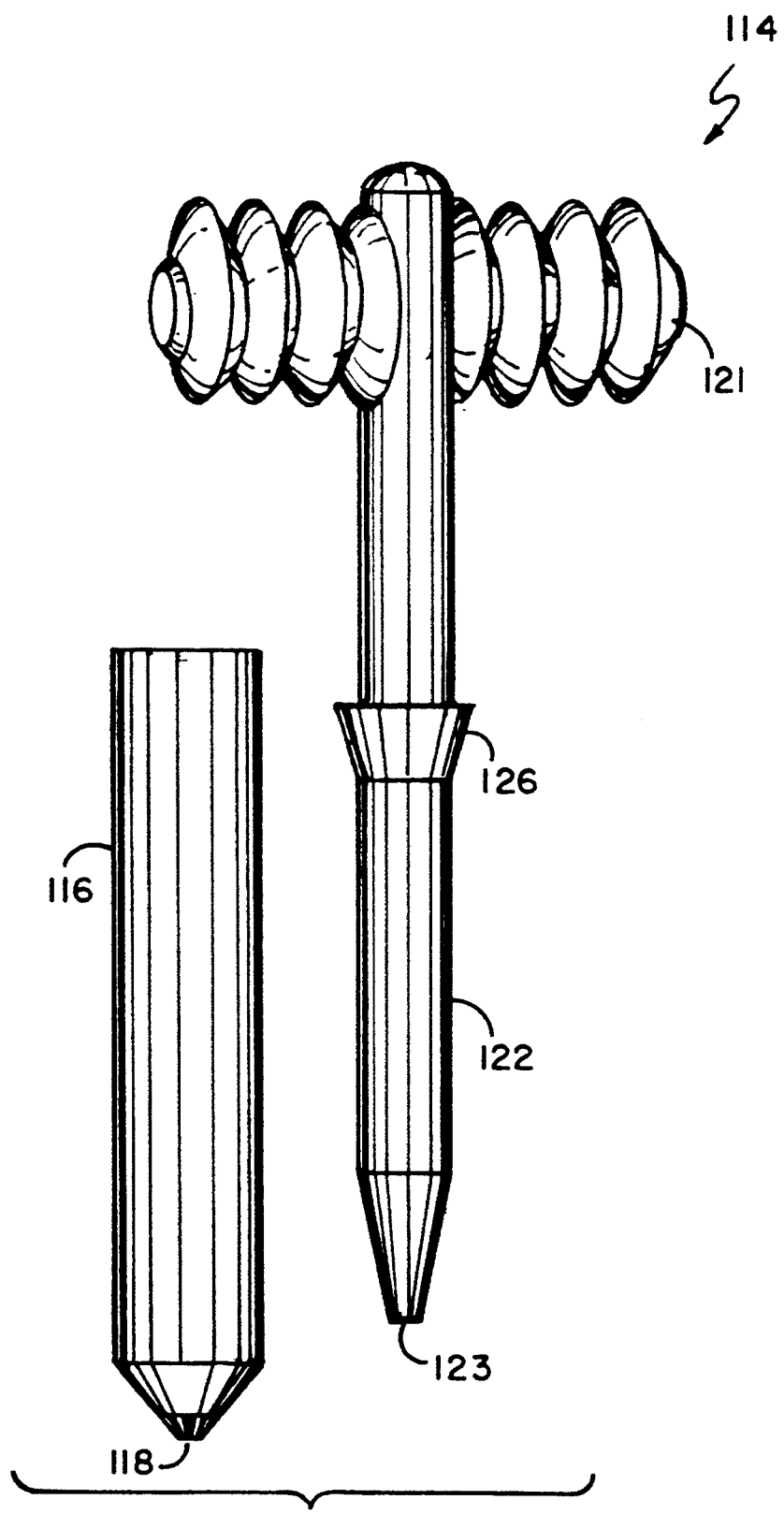
FIG. 12 illustrates schematically detail of the reaction device of FIG. 11.
Figure 13:
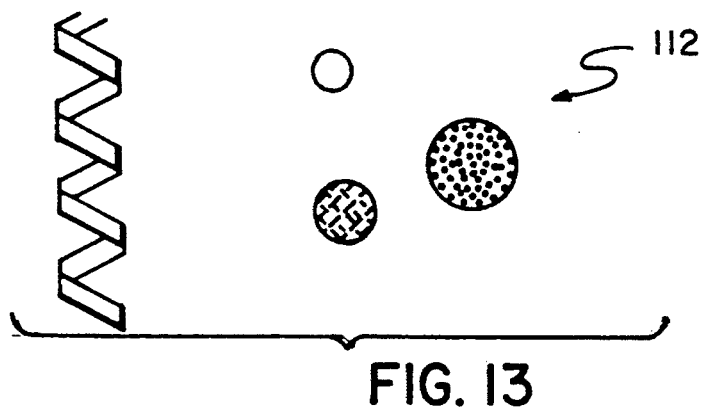
FIG. 13 illustrates a variety of solid support matrices for antibody immobilization in accordance with the invention.
Figure 14:
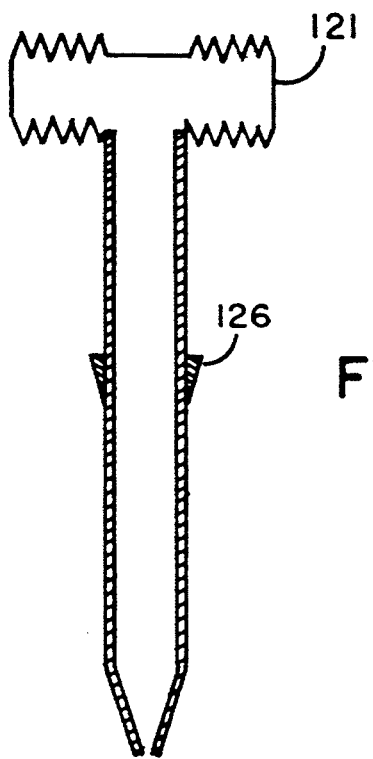
FIG. 14 is a vertical section of the collection-reaction pipette 114 of FIG. 12.
Figure 15:
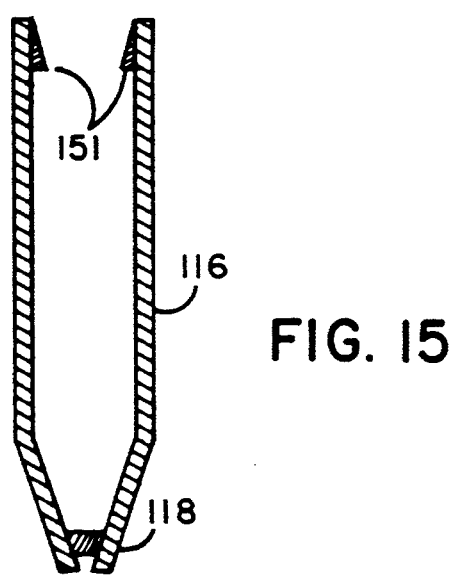
FIG. 15 is a vertical section of the docking device 116 of FIG. 12.

An alternative embodiment of a reaction device in accordance with the present invention is depicted as item 110 in FIGS. 11–15. FIG. 11 shows a docking assembly 116 of the device 110 in which the reaction pipette 114 of the device is docked. The docking assembly includes a filter 118 at its bottom. The reaction pipette 114 contains prepacked aliquots of antibodies immobilized, for example, on beads or a coiled strip (FIG. 13), or otherwise in the manner as discussed above in connection with FIG. 8. The reaction pipette 114 may be fabricated as a single piece of plastic or other suitable material, and includes, as shown in FIG. 12, an upper flexible bulb region 121, a reaction region 122, a locking position 126, and a port 123. Squeezing and releasing the bulb region 121 can supply positive and negative pressure differentials to the reaction region 122 so that fluid may be alternately drawn into and expelled from the reaction region 122 via the port 123. Although a flexible bulb is here shown as the source of positive and negative pressure differentials, other suitable sources may be employed. The reaction pipette 114 is employed by aspirating a sample of serum or plasma or blood by means of the bulb region 121 (FIGS. 12 and 14). The docking assembly 116 (which may be a modified pipette tip) is used to hold the collection-reaction pipette 114 during the immunoreaction (FIGS. 12 and 15). The docking assembly 116 contains an inner ring of resilient material on its inner surface 151, shown in FIG. 15 as a band around the upper lip of the assembly, to engage the locking position 126 of the reaction pipette 114; however, the resilient material may cover a larger portion of the inner surface thereof and may extend the entire length of the inner surface or a suitable proportion thereof. At the base of the docking assembly 116 (FIG. 15), suitable filter material 118 is positioned, during or post-manufacturing, to retain cells and crude debris.

Figure 16:
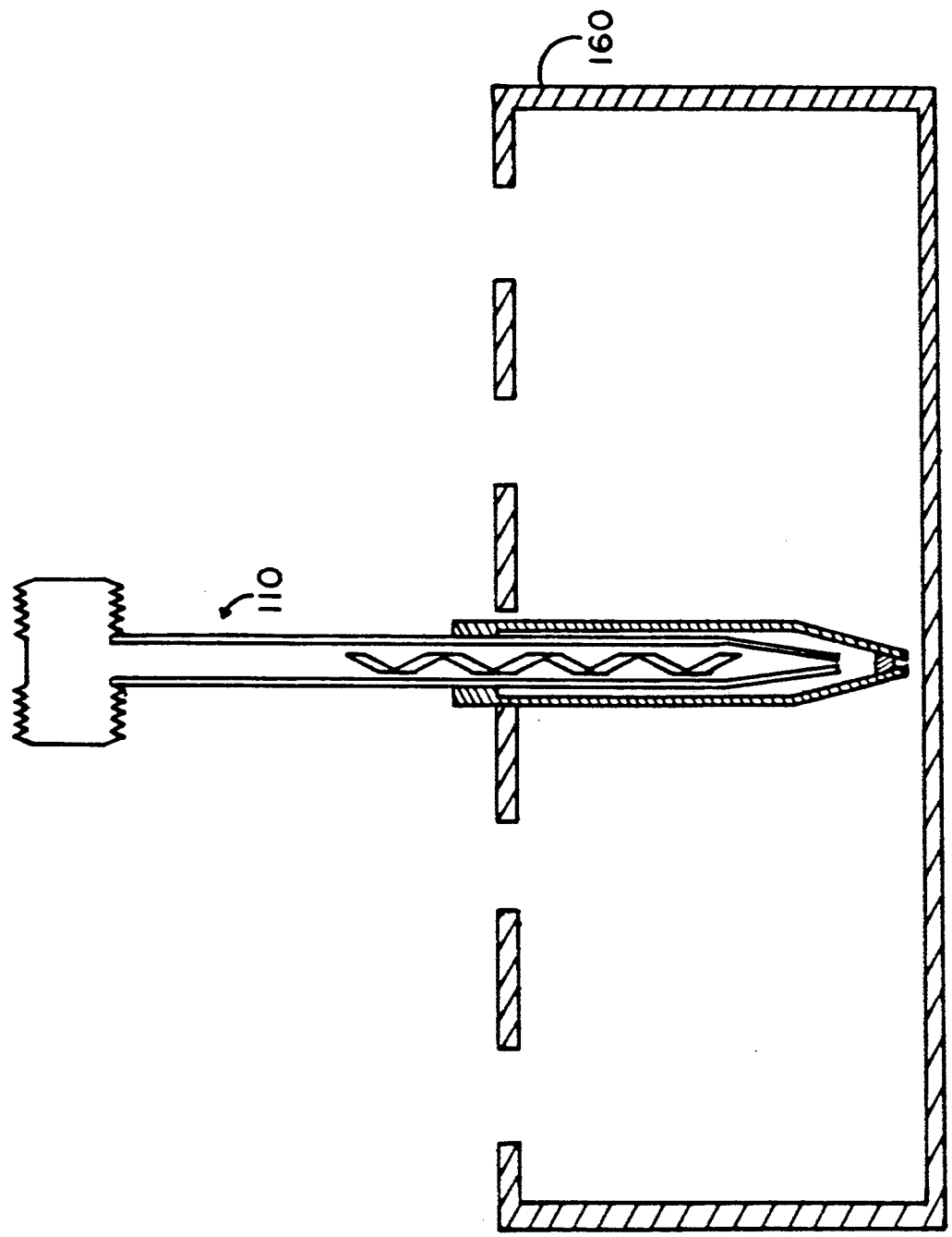
FIG. 16 is a vertical section of the reaction device of FIG. 11 loaded in a work station.

Operationally, the reaction pipette 114 is designed to aspirate a volume of liquid sample, by controlled compression of the flexible bulb portion 121 (FIG. 14); the aspirated sample is thereby brought into contact with the immobilized antibodies 112 within the reaction pipette 114; the reaction pipette 114 is then placed into the docking assembly 116 (FIGS. 12 and 15), where locking portion 126 engages against the inner ring 151. Mixing takes place, and the device 110 is then placed in the work station 160 (FIG. 16) for an appropriate incubation period.

At the completion of the incubation period, the device 110 may be removed from the work station 160 and the non-immunoreacted contents of the collection reaction pipette 114 are expelled from the pipette by compression of the flexible bulb region 121, through the filter 118, into a separate sample container which may be brought into position beneath the docking assembly 116.

Figure 17:
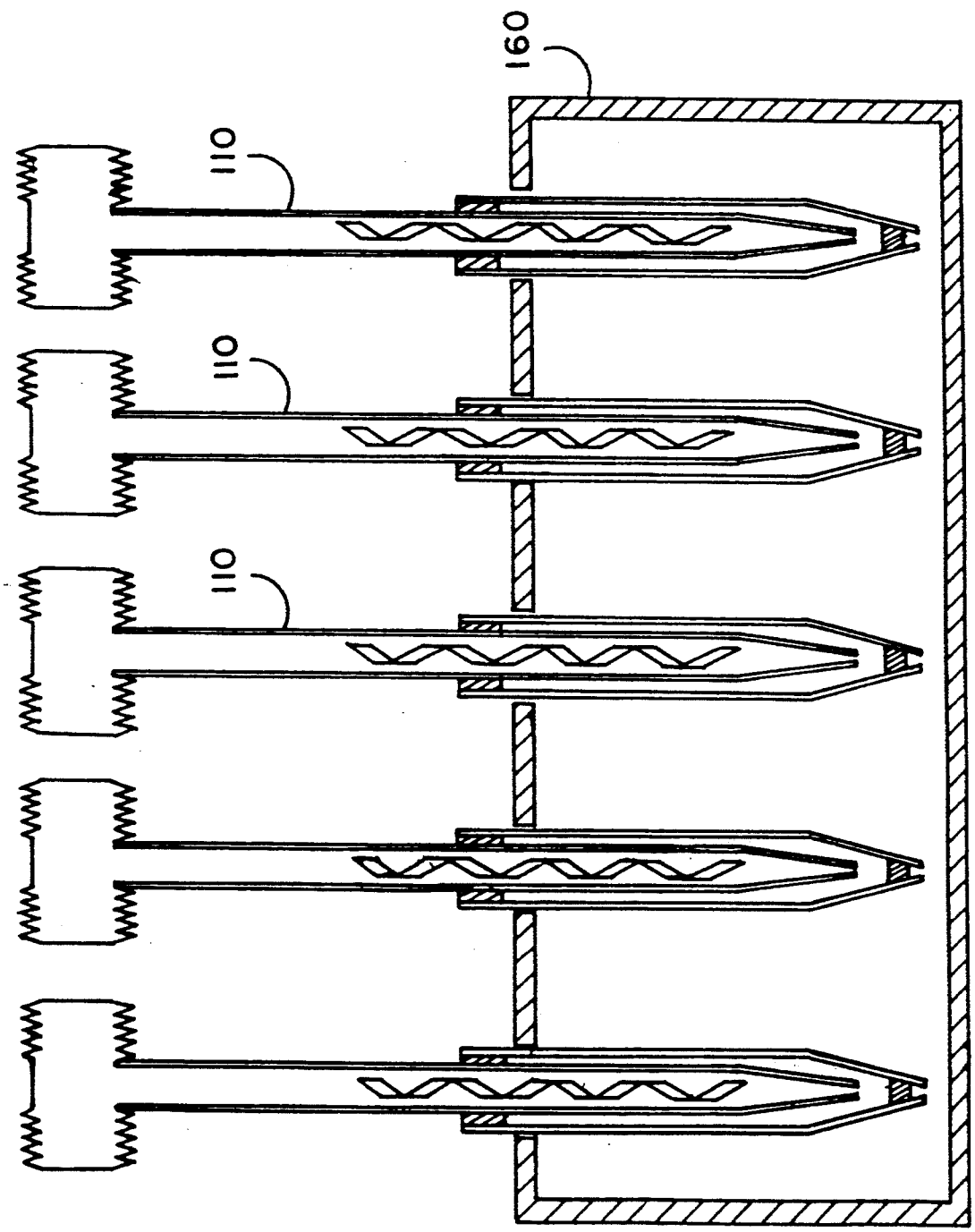
FIG. 17 is a fully loaded sample preparation system containing multiple units of the reaction device of FIG. 11 within a work station.

FIG. 17 illustrates a fully engaged sample preparation system, including a plurality of devices 110 oriented in a work station 160, which may be used in a kit format for the preparation of samples for analysis. The work station 160 and the device 110, and/or components of the device may be color coded to aid user recognition of alternative sample treatment systems.

Alternatively, the work station 160 may be modified so as to contain individual docking chambers into which individual reaction devices may be suspended during incubation and which may collect the filtrate from the expirated devices within the work station. Following sample expellation, the devices may be discarded and the collected filtrate may be analyzed.

FIG. 18 shows an embodiment of a reaction device 200, similar to that of FIGS. 11–17 but with certain enhancements. The device 200 includes a reaction pipette 202, a filter assembly 220, and a sample cup 206. The reaction pipette 202 (FIG. 19) contains aspiration bulb 204, antibodies bound to a support matrix 208, a molded ring 210 which holds the immobilized antibodies in place in the reaction pipette, and a fluid sample port 212 for entry and exit of the biological fluid sample. The filter assembly 220, shown in an exploded view in FIG. 20, includes a wiper 224, a filter retainer 226, a filter 228, and a filter carrier 230. Operation of this embodiment is similar to the operation of the embodiment described above in connection with FIGS. 11–17. The collected filtrate or immunoreactants can then be assayed using routine tests.

The efficacy of the embodiments of the reaction device illustrated above can be enhanced if one considers the effective volume of the reaction chamber in relation to the quantity of stabilized antibodies contained in the chamber. In particular, the relationship should be such that there are sufficient antibodies present to cause the target analyte to be completely immunoreacted and then removed from any anticipated biological fluid sample that may fill the effective volume of the reaction chamber. In addition to control of the effective volume of the reaction chamber by limiting its physical size, the effective volume of the reaction chamber may be limited in the embodiments of FIGS. 11–20 by limiting the maximum volume that can be displaced by squeezing the bulbs 121 or 204. The displacement can be limited in turn by limiting the bulb size or imposing physical constraints on the amount the bulb may be squeezed, for example, by inserting a large solid object into the bulb.

Although the foregoing discussion has been principally directed toward devices containing immobilized antibodies, it is only necessary that the antibodies be suitably stabilized and contained within the reaction chamber at the time of the immunoseparation reaction. Thus freeze dried antibodies may be contained in a water-soluble or permeable structure in the reaction chamber. Alternatively, the antibodies may be stored in a liquid suspension in a container in fluid communication with the reaction chamber, in such a way that they are put in contact with the biological fluid sample when the device is used. The container could be ruptured at the time of use, or the reaction chamber can be designed to hold the suspension sealed from the environment until the device is used.

Although the above discussion has been with respect primarily to the detection of cholesterol in specific lipoprotein classes, the invention is also widely applicable to the detection of a targeted analyte in a class of analytes, such as targeted isozymes of an enzyme in the presence of other isozymes and targeted immunoglobulins in the presence of non-targeted immunoglobulins. For example, the invention is applicable to targeted isozymes of creatine kinase, lactate dehydrogenase, amylase, and alkaline and acid phosphatases. The invention may be implemented in a manner similar to that described above in the case of cholesterol testing, except that the antibodies used in the reaction devices of FIGS. 7 through 20 must be antibodies to the non-targeted analyte, following the immunoseparation. The antibodies may be prepared using methods known in the art.

It can be seen, however, that if the targeted analyte is separated from the non-targeted analytes in the applicable class of analytes, and there exists a routine test for the class of analytes, then following separation in accordance with the invention, the targeted analyte can be assayed using the routine test for the class of analytes. For example, one may use a routine test for amylase to detect pancreatic specific amylase if the invention is employed as a "front end" to the routine test. In other words, embodiment of the invention may be employed to separate pancreatic specific amylase from other isozymes of amylase, achieving separation, for example, using antibodies to all isozymes of amylase other than pancreatic specific amylase. Thereafter the filtrate may be assayed using the routine test to identify the level of pancreatic specific amylase in the sample. A similar strategy may be used to assay any targeted analyte in a class of analytes for which a routine test exists.

The invention may also be used to remove substances such as bilirubin and hemoglobin that can interfere with spectrophotometric or other assays for an analyte. In such instances, antibodies to bilirubin and hemoglobin may be employed to achieve their immunoseparation (using the invention) from the sample prior to conduct of an assay in accordance with prior art techniques.

It can be seen that the antibodies employed in the invention need not be restricted to those for a particular molecule, since any undesired substances may be immuno-separated in accordance with the invention, as long as undesired cross reactions are avoided.

What is claimed is:

1. A method for measuring a cholesterol analyte in a targeted lipoprotein class in a biological fluid in the presence of at least one cholesterol-containing interfering substance in another lipoprotein class, comprising:

(i) obtaining a disposable reaction device having a reaction chamber, the reaction chamber containing immobilized antibodies which are specific for said interfering substance for removal of the interfering substance from a biological fluid;

(ii) adding the biological fluid sample to the reaction chamber of the device for reaction with said antibodies, wherein the immobilized antibodies bind to the interfering substance without reacting with the cholesterol analyte;

(iii) causing the non-reactants from step (ii), including the cholesterol analyte, to be removed from the reaction device into a collection chamber, wherein the reacted interfering substance remains in the reaction chamber of the reaction device; and (iv) conducting a clinical assay for the cholesterol analyte on the non-reactants including the cholesterol analyte.

2. A method according to claim 1, wherein a suitable volume of antibodies has been predetermined in relation to a volume of the reaction chamber, the amount of antibodies added to the reaction chamber is sufficient to immuno-react with substantially all of the interfering substance to remove the interfering substance from any anticipated biological fluid sample that may fill the volume of the reaction chamber.

3. A method according to claim 1, wherein step (iii) includes the step of immobilizing the antibodies.

4. A method according to claim 1, wherein step (iii) includes the step of freeze drying the antibodies.

5. A method according to claim 1, wherein the reaction device further includes filter means, for filtering components in the reaction chamber, in fluid communication with the reaction chamber.

6. A method according to claim 5,
   wherein the reaction chamber includes a first port for receiving a biological fluid sample, a second port for accessing components in the reaction chamber;
   wherein the filter means includes a filter disposed in the reaction chamber between the first and second ports;
   wherein the device further includes a collection chamber in fluid communication with the second port;
   such method further comprising, prior to step (vii), centrifuging the device and allowing the filter to separate the immuno-reactants from the non-reactants which pass into the collection chamber as filtrate.

7. A method according to claim 6, wherein the antibodies are stabilized by immobilizing the antibodies on an insoluble carrier.

8. A method according to claim 6, wherein the antibodies are stabilized by immobilizing the antibodies on a soluble high molecular weight carrier.

9. A method according to claim 6, wherein the antibodies are stabilized by freeze drying.

10. A method according to claim 1,
    wherein the reaction chamber has first and second ports;
    wherein the reaction device includes differential pressure means in fluid communication with the first port for supplying positive and negative pressure differentials to the reaction chamber so that fluid may be alternately drawn into and expelled from the reaction chamber via the second port; and
    wherein step (iv) includes drawing the biological fluid sample into the reaction chamber using the differential pressure means.

11. A method according to claim 6, wherein the antibodies are stabilized by immobilizing the antibodies on an insoluble carrier.

12. A method according to claim 10, wherein the antibodies are stabilized by immobilizing the antibodies on a soluble high molecular weight carrier.

13. A method according to claim 6, wherein the step of stabilizing the antibodies are stabilized by freeze drying.

14. A method according to claim 10, wherein the reaction device includes a filter assembly removably attachable to the reaction chamber, the method further comprising prior to step (v), the step of expelling the components in the reaction chamber into the filter assembly using the differential pressure means.

15. A method for measuring a cholesterol analyte in a targeted lipoprotein class in a biological fluid in the presence of at least one cholesterol-containing interfering substrate in another lipoprotein class, comprising:
   (i) selecting a disposable reaction device having a reaction chamber;
   (ii) immobilizing antibodies which are specific for said interfering substance to an interior wall of said reaction chamber;
   (iii) adding a biological fluid sample to the reaction chamber of the device for reaction with said antibodies, wherein the antibodies bind to the interfering substance without reacting with the cholesterol analyte;
   (iv) separating the non-reactants from step (iii), including the cholesterol, analyte from the interfering substance; and
   (v) conducting an assay for the cholesterol analyte on the non-reactants including the cholesterol analyte.

16. A method for measuring a cholesterol analyte in a targeted lipoprotein class in a biological fluid in the presence of at least one cholesterol-containing interfering substance in another lipoprotein class, comprising:
   (i) obtaining a disposable reaction device having a reaction chamber, the reaction chamber containing antibodies which are specific for said interfering substance for removal of the interfering substance from a biological fluid;
   (ii) adding the biological fluid sample to the reaction chamber of the disposable reaction device for reaction with said antibodies wherein said antibodies bind to said interfering substance without reacting with the cholesterol analyte;
   (iii) separating non-reactants including the cholesterol analyte from bound interfering substance by filtration; and
   (iv) conducting an assay for the cholesterol analyte on the filtrate, wherein the filtrate includes the cholesterol analyte.

* * * * *

UNITED STATES PATENT AND TRADEMARK OFFICE
CERTIFICATE OF CORRECTION

PATENT NO. : 5,403,745
DATED : April 4, 1995
INVENTOR(S) : Ollington, Byrnes and Pogorzelski It is certified that error appears in the above-indentified patent and that said Letters Patent is hereby corrected as shown below:

Column 17, Line 6          "substrate"  should be --substance--

Signed and Sealed this

Twenty-fifth Day of July, 1995

Attest:

BRUCE LEHMAN

Attesting Officer    Commissioner of Patents and Trademarks